US009074254B2

(12) United States Patent
Lavedan et al.

(10) Patent No.: US 9,074,254 B2
(45) Date of Patent: Jul. 7, 2015

(54) METHOD OF PREDICTING A PREDISPOSITION TO QT PROLONGATION

(75) Inventors: Christian Lavedan, Potomac, MD (US); Simona Volpi, Derwood, MD (US); Louis Licamele, Gaithersburg, MD (US); Kendra Tomino Mack, Westminster, MD (US); Callie Michelle Heaton, Washington, DC (US)

(73) Assignee: Vanda Pharmaceuticals, Inc., Washington, DC (US)

( * ) Notice: Subject to any disclaimer, the term of this patent is extended or adjusted under 35 U.S.C. 154(b) by 1370 days.

(21) Appl. No.: 12/593,419

(22) PCT Filed: Mar. 28, 2008

(86) PCT No.: PCT/US2008/058791
§ 371 (c)(1),
(2), (4) Date: Dec. 28, 2009

(87) PCT Pub. No.: WO2008/121899
PCT Pub. Date: Oct. 9, 2008

(65) Prior Publication Data
US 2010/0226858 A1 Sep. 9, 2010

Related U.S. Application Data

(60) Provisional application No. 60/908,734, filed on Mar. 29, 2007.

(51) Int. Cl.
C12Q 1/68 (2006.01)

(52) U.S. Cl.
CPC ........ *C12Q 1/6883* (2013.01); *C12Q 2600/156* (2013.01); *C12Q 2600/136* (2013.01)

(58) Field of Classification Search
CPC . A61K 31/519; A61K 23/00; A61K 31/7052; A61K 31/496; A61K 31/137; A61K 31/5513; A61K 31/047; A61K 31/164; A61K 31/355; C12Q 1/6883; C12Q 2600/106
See application file for complete search history.

(56) References Cited

U.S. PATENT DOCUMENTS

| 5,364,866 | A | 11/1994 | Strupczewski et al. |
| 5,658,911 | A | 8/1997 | Strupczewski et al. |
| 6,140,345 | A | 10/2000 | Strupczewski et al. |
| 6,908,734 | B2 | 6/2005 | Dragic et al. |
| 2003/0170176 | A1 | 9/2003 | Leyland-Jones |
| 2004/0091909 | A1 | 5/2004 | Huang |
| 2004/0096874 | A1 | 5/2004 | Neville et al. |
| 2006/0073506 | A1* | 4/2006 | Christians et al. ............ 435/6 |

FOREIGN PATENT DOCUMENTS

| WO | 9309276 | A1 | 5/1993 |
| WO | 9511680 | A1 | 5/1995 |
| WO | 03020707 | A1 | 3/2003 |
| WO | 03038123 | A2 | 5/2003 |
| WO | 03044226 | A2 | 5/2003 |
| WO | 2004058052 | A2 | 7/2004 |
| WO | 2006039663 | A2 | 4/2006 |
| WO | 2007035953 | A2 | 3/2007 |

OTHER PUBLICATIONS

Volpi et al; Molecular Psychiatry, vol. 14, pp. 1024-1031, 2009.*
ss 1451062 (rs993648, Oct. 2000, dbSNP, NCBI, NLM).*
Tuson et al; American Journal of Human Genetics, vol. 74 pp. 128-138, 2004.*
Juppner; Bone, vol. 17; 1995, pp. 39S-40S.*
Lucentini (The Scientist; 2004, vol. 24, p. 20).*
Hegele (Arterioscler. Thromb. Vasc. Biol.; 2002, vol. 22, pp. 1058-1061).*
Levine et al; Formulary Journal, Jun. 1, 2008, pp. 1-7.*
Volpi et al; 57th Annual meeting of the American Society of Human Genetics, 2007, Abstract.*
Heaton et al., "Whole-genome association study identifies polymorphisms in the CERKL gene associated with QT prolongation during iloperidone treatment of patients with schizophrenia," Oct. 2007, 1 page, American Society of Human Genetics 57th Annual Meeting (XP002500472).
Volpi et al., "Whole genome association study identifies polymorphisms associated with QT prolongation during iloperidone treatment of schizophrenia," Jun. 2008, pp. 1-8, Molecular Psychiatry (XP002500473).
NCBI Online Database, "Single Nucleotide Polymorphism," Sep. 2000, 6 pages, RefSNP #: rs895901 (XP002500474), http://www.ncbi.nlm.nih.gov/SNP/snp_ss.cgi?subsnp_id=1326361.
NCBI Online Database, "Single Nucleotide Polymorphism," Jul. 2003, 7 pages, RefSNP #: rs1441162 (XP002500475), http://www.ncbi.nlm.nih.gov/SNP/snp_ss.cgi?subsnp_id=11451915.
NCBI Online Database, "Single Nucleotide Polymorphism," Jun. 2003, pp. 1-6, RefSNP #: rs6433927 (XP002500476), http://www.ncbi.nlm.nih.gov/SNP/snp_ss.cgi?subsnp_id=9936521.
NCBI Online Database, "Single Nucleotide Polymorphism," Nov. 2007, 3 pages, RefSNP #: rs16867450 (XP002500477), http://www.ncbi.nlm.nih.gov/SNP/snp_ss.cgi?subsnp_id=84544314.
NCBI Online Database, "Single Nucleotide Polymorphism," Oct. 2007, pp. 1-3, RefSNP #: rs16867452 (XP002500478), http://www.ncbi.nlm.nih.gov/SNP/snp_ss.cgi?subsnp_id=79032989.
NCBI Online Database, "Single Nucleotide Polymorphism," Nov. 2007, 3 pages, RefSNP #: rs993648 (XP002500479), http://www.ncbi.nlm.nih.gov/SNP/snp_ss.cgi?subsnp_id=83108969.
NCBI Online Database, "Single Nucleotide Polymorphism," Nov. 2007, 3 pages, RefSNP #: rs993650 (XP002500480), http://www.ncbi.nlm.nih.gov/SNP/snp_ss.cgi?subsnp_id=86142829.
Patent Cooperation Treaty, PCT Notification Concerning Transmittal of International Preliminary Report on Patentability and Written Opinion of the International Searching Authority, for International Application No. PCT/US2008/058791 dated Oct. 8, 2009, 10 pages.
Patent Cooperation Treaty, PCT Notification Concerning Transmittal of International Search Report and the Written Opinion of the International Searching Authority, or the Declaration, for International Application No. PCT/US2008/058791 dated Nov. 7, 2008, 19 pages.

* cited by examiner

*Primary Examiner* — Jehanne Sitton
(74) *Attorney, Agent, or Firm* — Hoffman Warnick LLC

(57) ABSTRACT

The present invention describes an association between genetic polymorphisms in the ceramide kinase-like (CERKL) gene and a predisposition to prolongation of the QT interval, and provides related methods for the prediction of such a predisposition, the administration of QT interval-prolonging compounds to individuals having such a predisposition, and determining whether a compound is capable of inducing QT prolongation.

6 Claims, No Drawings

METHOD OF PREDICTING A PREDISPOSITION TO QT PROLONGATION

CROSS-REFERENCE TO RELATED APPLICATIONS

This application claims the benefit of co-pending U.S. Provisional Patent Application No. 60/908,734, filed 29 Mar. 2007, which is hereby incorporated herein.

SEQUENCE LISTINGS

The sequence listings contained in the electronic file titled "VAND-0042-PCT_sequence_listings.txt," created 28 Mar. 2008, comprising 4.1 MB, is hereby incorporated herein.

BACKGROUND OF THE INVENTION

1. Technical Field

The invention relates generally to a method of predicting an individual's predisposition to QT prolongation, and more particularly, to a method of predicting such predisposition based on a sequence of the individual's ceramide kinase-like (CERKL) gene.

2. Background

Prolongation of the electrocardiographic QT interval (the time between the start of the Q wave and the end of the T wave) is referred to as long QT syndrome (LQTS). LQTS may comprise a genetic component. In some patients with LQTS, QT prolongation can be a chronic condition. In some persons, LQTS may be induced by the administration of an active pharmaceutical ingredient that prolongs the QT interval.

A number of compounds are believed to be capable of prolonging the QT interval. These include amiodarone, arsenic trioxide, bepridil, chloroquine, chlorpromazine, cisapride, clarithromycin, disopyramide, dofetilide, domperidone, droperidol, erythromycin, halofantrine, haloperidol, ibutilide, iloperidone, levomethadyl, mesoridazine, methadone, pentamidine, pimozide, procainamide, quinidine, sotalol, sparfloxacin, and thioridazine.

Other compounds are suspected of being capable of prolonging the QT interval, although such prolongation has not been definitively established. These include alfuzosin, amantadine, azithromycin, chloral hydrate, clozapine, dolasetron, felbamate, flecamide, foscarnet, fosphenyloin, gatifloxacin, gemifloxacin, granisetron, indapamide, isradipine, levofloxacin, lithium, moexipril, moxifloxacin, nicardipine, octreotide, ofloxacin, ondansetron, quetiapine, ranolazine, risperidone, roxithromycin, tacrolimus, tamoxifen, telithromycin, tizanidine, vardenafil, venlafaxine, voriconazole, and ziprasidone.

Individuals at risk of suffering LQTS are advised not to use still other compounds, due to the possibility that they may prolong the QT interval. These include albuterol, amitriptyline, amoxapine, amphetamine, dextroamphetamine, atomoxetine, chloroquine, ciprofloxacin, citalopram, clomipramine, cocaine, desipramine, dexmethylphenidate, dobutamine, dopamine, doxepin, ephedrine, epinephrine, fenfluramine, fluconazole, fluoxetine, galantamine, imipramine, isoproterenol, itraconazole, ketoconazole, levalbuterol, metaproterenol, methylphenidate, mexiletine, midodrine, norepinephrine, nortriptyline, paroxetine, phentermine, phenylephrine, phenylpropanolamine, protriptyline, pseudoephedrine, ritodrine, salmeterol, sertraline, sibutramine, solifenacin, terbutaline, tolterodine, trimethoprim-sulfa, and trimipramine.

The CERKL gene has been mapped by Tuson et al. to 2q31.2-q32.3, between the ITGA4 gene and the NEUROD1 gene, and determined to contain 13 exons. Tuson et al., *Mutations of CERKL, a novel human ceramide kinase gene, causes autosomal recessive retinitis pigmentosa (RP26)*, Am. J. Hum. Genet. 74: 128-138, 2004. PubMed ID: 14681825. Ceramide kinases convert the sphingolipid metabolite ceramide into ceramide-1-phosphate, both of which mediate cellular apoptosis.

SUMMARY OF THE INVENTION

The present invention describes an association between genetic polymorphisms in the ceramide kinase-like (CERKL) gene and a predisposition to prolongation of the QT interval, and provides related methods for the diagnosis of such predisposition and for the administration of QT interval-prolonging compounds to individuals having such a predisposition.

A first aspect of the invention provides a method of administering to an individual a compound capable of prolonging the individual's QT interval (e.g., a compound the administration has been linked to prolonged QT, such as in clinical studies in humans), the method comprising: determining at least a portion of an individual's ceramide kinase-like (CERKL) gene sequence; and in the case that a portion of the individual's CERKL gene sequence is associated with an increased risk of QT prolongation, administering to the individual a quantity of the compound less than would be administered to an individual having a CERKL gene sequence not associated with an increased risk of QT prolongation, or electing instead to treat the individual with a different compound not known to be associated with QT prolongation.

A second aspect of the invention provides a method of determining whether or not an individual is predisposed to prolongation of the QT interval, the method comprising: determining at least a portion of an individual's ceramide kinase-like (CERKL) gene sequence. All or a portion, including a SNP described hereinbelow, can be compared to CERKL gene sequences that are associated with QT prolongation.

A third aspect of the invention provides a method of administering a compound capable of prolonging QT interval to an individual suffering from long QT syndrome (LQTS), the method comprising: determining at least a portion of an individual's ceramide kinase-like (CERKL) gene sequence; and administering to the individual a quantity of the compound based on the individual's CERKL gene sequence.

A fourth aspect of the invention provides a method of administering to an individual a compound capable of prolonging the individual's QT interval, the method comprising: characterizing an expression product of an individual's ceramide kinase-like (CERKL) gene; and in the case that the characterized expression product is associated with an increased risk of QT prolongation, administering to the individual a quantity of the compound less than would be administered to an individual having a CERKL gene expression product not associated with an increased risk of QT prolongation. Expression products of the CERKL gene may include, for example, mRNA and protein including any isoform of the mRNA and protein.

fifth aspect of the invention provides a method of determining whether an individual is predisposed to prolongation of the QT interval, the method comprising: characterizing an expression product of an individual's ceramide kinase-like (CERKL) gene. All or a portion of the gene expression product can be compared to CERKL gene expression products that are associated with QT prolongation.

A sixth aspect of the invention provides a method of administering a compound capable of prolonging a QT interval to an individual suffering from long QT syndrome (LQTS), the method comprising: characterizing an expression product of an individual's ceramide kinase-like (CERKL) gene; and administering to the individual a quantity of the compound based on the characterized expression product.

A seventh aspect of the invention provides a method of determining whether a compound is capable of prolonging QT interval in an individual, the method comprising: measuring an expression product of the individual's ceramide kinase-like (CERKL) gene; administering to the individual a quantity of the compound; remeasuring the expression product of the individual's CERKL gene; and determining whether the compound is capable of prolonging the individual's QT interval based on a difference in the measurements of the expression product of the individual's CERKL gene.

An eighth aspect of the invention provides a method of determining whether a compound is capable of prolonging a QT interval in an individual, the method comprising: measuring a QT interval of each of a plurality of test organisms, the plurality including a first test organism having a ceramide kinase-like (CERKL) genotype associated with a predisposition for prolongation of QT interval and a second organism having a CERKL genotype not associated with a predisposition for prolongation of QT interval; administering a quantity of the compound to each of the plurality of test organisms; remeasuring a QT interval of at least the first test organism; and determining that the compound is capable of prolonging a QT interval in an individual in the case that the remeasured QT interval is greater than the measured QT interval. Test organisms may include, for example, humans, animal models, and/or cell lines.

In further aspects of the inventions, the invention comprises method for determining an individual's genotype for the CERKL gene that comprises determining the individual's genotype at least one single nucleotide polymorphism (SNP) locus selected from the group consisting of: rs895901, rs1441162, rs993650, rs993648, rs16867450, rs16867452, and rs6433927, as well as a method for reporting a person's genotype for the CERKL gene that comprises determining and reporting the individual's genotype at least one single nucleotide polymorphism (SNP) locus selected from the group consisting of: rs895901, rs1441162, rs993650, rs993648, rs16867450, rs16867452, and rs6433927.

DETAILED DESCRIPTION OF THE INVENTION

As indicated above, the invention provides a method of predicting an individual's, e.g., a human subject's, predisposition to QT prolongation based on the sequence of the individual's ceramide kinase-like (CERKL) gene.

A number of single nucleotide polymorphisms (SNPs) within the CERKL gene have been found to have a significant correlation to a predisposition to drug-induced QT prolongation. Table 1, below, shows such SNPs and the genotypes associated with QT prolongation following the administration of iloperidone.

TABLE 1

CERKL SNP Genotypes and QT Prolongation Following Administration of Iloperidone

| Affymetrix SNP No. | rs number[1] | Position | Flank | Orientation | Lowest QTc change | P value[3] | Allele A | Allele B | Seq. ID No. |
|---|---|---|---|---|---|---|---|---|---|
| SNP_A-2220578 | rs17226490 | 142613 | ccttcttccaaaaaaa[C/G]ttggagatccctgttc | forward | Non-AA | 0.230510123 | A | G | 1 |
| SNP_A-191199 | rs16867442 | 142502 | tgtgagaagttacata[A/C]aatagtgatactgtag | reverse | AB | 0.523235967 | A | C | 2 |
| SNP_A-1937552 | rs718449 | 141189 | ttgaactccacacttg[C/T]accatcatggcactcc | forward | AB | 0.222483417 | C | T | 3 |
| SNP_A-1950600 | rs12623737 | 132230 | tttcatctgaacattg[A/C]agaatgacatctacat | forward | AB | 0.077895801 | A | C | 4 |
| SNP_A-4262423 | rs10514624 | 128459 | ctgtgagtttgaagta[C/T]ggtgggtatgcccaag | reverse | AB | 0.415376626 | C | T | 5 |
| SNP_A-1966128 | rs10490688 | 124294 | caaatacaattcagag[A/C]ccttactgtggcatgt | reverse | AB | 0.007281497 | A | C | 6 |
| SNP_A-2246382 | rs16867447 | 121205 | ctggttctactggtaa[A/T]ctgttttcaaaataa | forward | AB | 0.059152747 | A | T | 7 |
| SNP_A-1966129 | rs6706370 | 118832 | actgttaaaccttatg[A/T]gagcttcagattctatat | forward | Non-AA | 0.136332739 | A | T | 8 |
| SNP_A-2140582 | rs895901 | 109658 | tgctctgtgttcaacat[A/T]gtgcaggatgcgagatg | forward | AB | 0.004039676 | A | T | 9 |
| SNP_A-1937875 | rs1441162 | 91975 | ttgaatcatttgcgcc[A/C]aggaactggacagacc | forward | AA | 0.003384913 | A | C | 10 |
| SNP_A-2122170 | rs993650 | 90904 | agtgatttccagtata[C/T]gctgttaagtttaaaa | reverse | AB | 4.83E-07 | C | T | 11 |
| SNP_A-4232718 | rs993648 | 90758 | cccettataggtaacc[A/G]attgcactggtttcta | forward | AB | 2.60E-07 | A | G | 12 |

TABLE 1-continued

CERKL SNP Genotypes and QT Prolongation Following Administration of Iloperidone

| Affymetrix SNP No. | rs number[1] | Position | Flank | Orientation | Lowest QTc change | P value[3] | Allele A | Allele B | Seq. ID No. |
|---|---|---|---|---|---|---|---|---|---|
| SNP_A-2216593 | rs16867450 | 89951 | cctctatatctcaaag[A/G] aaactcaatttcaact | reverse | Non-AA | 0.004139028 | A | G | 13 |
| SNP_A-2216297 | rs16867452 | 86371 | cctcctctaccatcta[C/T] cggttgtttaaccttg | reverse | BB | 0.005241705 | C | T | 14 |
| SNP_A-1827109 | rs6433927 | 60587 | tggcttcctctaattt[C/G] tactccaaaatggtt | forward | Non-AA | 0.001479588 | C | G | 15 |
| SNP_A-1966130 | rs10497581 | 53701 | tcttctcccaataggt[A/G] aagtacgacagagctc | forward | Non-AA | 0.52388901 | A | G | 16 |
| SNP_A-2310431 | rs13398869 | 42469 | ggaactgtcttaaaag[C/T] ctgaaagaagtcagat | reverse | Non-BB | 0.075041974 | C | T | 17 |
| SNP_A-1893037 | rs1967351 | 26643 | tgcactgtaggttaaa[C/T] tggctctttgggctaa | reverse | Non-BB | 0.258267198 | C | T | 18 |
| SNP_A-4275669 | rs10207791 | 23890 | aatggggaagcagtca[A/G] gaagaaagtgagtccc | reverse | Non-AA | 0.138169504 | A | G | 19 |
| SNP_A-2065238 | rs2696344 | 13541 | aattggcttctcttaa[C/G] tatatgagatagggtt | forward | Non-BB | 0.086456719 | C | G | 20 |
| SNP_A-1966131 | rs12053195 | 6069 | actagtactgtcccag[A/G] aaaatttatacacctt | forward | Non-AA | 0.399257392 | A | G | 21 |
| | | 77898 | cagtgtctgttgttcct[C/T] tctatgaaacacaatgg | forward | A/B | 0.0047 | T | C | 22 |
| | rs6433923 | 77934 | taattggaaaattta[T/A]t tttttttcaggtg | forward | A/B | 0.0045 | T | A | 23 |
| | | 77949 | tttttttcaggtg[A/C]tt ctaagtatgacttgc | forward | A/B | 0.2241 | A | C | 24 |

The following SNP genotypes were found to most accurately predict a predisposition to QT prolongation: non-AT at rs895901, non-AA at rs1441162, non-CT at rs993650, non-AG at rs993648, AA at rs16867450, non-TT at rs16867452, and CC at rs6433927. These genotypes are included amongst all genotypes associated with a predisposition to QT prolongation. Therefore, individuals possessing one or more of these genotypes may be considered predisposed to QT prolongation following the administration of a compound capable of prolonging the QT interval.

Since the QT interval changes with changes in heart rate, the QT interval is often measured as a corrected QT (QTc) interval. Any number of formulas may be employed to calculate the QTc, including, for example, the Fridericia formula (QTcF), the Bazett formula (QTcB), and the Rautaharju formula (QTp), among others. In the studies described herein, QT was calculated using the Fridericia formula. However, the present invention includes the use of any such formula or method for calculating a QTc or an uncorrected QT.

As noted above, a large number of compounds are known or suspected to be capable of inducing QT prolongation in some individuals, including individuals not suffering from LQTS. One such compound is iloperidone. Iloperidone is disclosed in U.S. Pat. Nos. 5,364,866, 5,658,911, and 6,140,345, each of which is incorporated herein by reference. Metabolites of iloperidone may also be capable of prolonging a QT interval. Metabolites of Iloperidone, e.g., 1-[4-[3-[4-(6-Fluoro-1,2-benzisoxazol-3-yl)-1-piperidinyl]propoxy]-3-methoxyphenyl]ethanol, are described in International Patent Application Publication No. WO03020707, which is also incorporated herein by reference.

Other iloperidone metabolites include: 1-[4-[3-[4-(6-Fluoro-1,2-benzisoxazol-3-yl)-1-piperidinyl]propoxy]-3-hydroxyphenyl]ethanone; 1-[4-[3-[4-(6-Fluoro-1,2-benzisoxazol-3-yl)-1-piperidinyl]propoxy]-3-methoxyphenyl]-2-hydroxyethanone; 4-[3-[4-(6-Fluoro-1,2-benzisoxazol-3-yl)-1-piperidinyl]propoxy]-3-hydroxy-α-methylbenzene methanol; 4-[3-[4-(6-Fluoro-1,2-benzisoxazol-3-yl)-1-piperidinyl]propoxyl-2-hydroxy-5-methoxy-α-methylbenzenemethanol; 1-[4-[3-[4-(6-Fluoro-1,2-benzisoxazol-3-yl)-1-piperidinyl]propoxy]-2-hydroxy-5-methoxyphenyl] ethanone; and 1-[4-[3-[4-(6-Fluoro-1,2-benzisoxazol-3-yl)-1-piperidinyl]propoxy]-2,5-dihydroxyphenyl]ethanone. See U.S. Pat. No. 5,364,866 and International Patent Application Publication Nos. WO9309276 and WO9511680, which are incorporated herein by reference.

In some embodiments of the invention, a compound known or suspected to be capable of inducing QT prolongation has the formula:

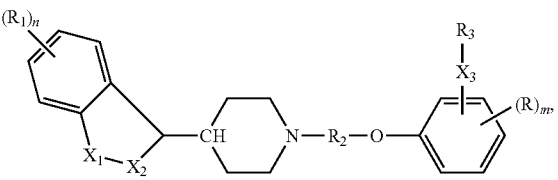

(1)

wherein: R is, independently, hydrogen, lower alkyl, lower alkoxy, hydroxyl, carboxyl, lower hydroxyketone, lower alkanol, hydroxyl acetic acid, pyruvic acid, ethanediol, chlorine, fluorine, bromine, iodine, amino, lower mono or dialkylamino, nitro, lower alkyl thio, trifluoromethoxy, cyano, acylamino, trifluoromethyl, trifluoroacetyl, aminocarbonyl, monoaklylaminocarbonyl, dialkylaminocarbonyl, formyl,

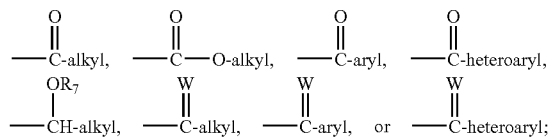

alkyl is lower alkyl, branched or straight and saturated or unsaturated; acyl is lower alkyl or lower alkyloxy bonded through a carbonyl; aryl is phenyl or phenyl substituted with at least one group, $R_5$, wherein each $R_5$ is, independently, hydrogen, lower alkyl, lower alkoxy, hydroxy, chlorine, fluorine, bromine, iodine, lower monoalkylamino, lower dialkylamino, nitro, cyano, trifluoromethyl, or trifluoromethoxy; heteroaryl is is a five- or six-membered aryl ring having at least one heteroatom, $Q_3$, wherein each $Q_3$ is, independently, —O—, —S—, —N(H)—, or —C(H)=N—, W is $CH_2$ or $CHR_8$ or N—$R_9$; $R_1$ is —H, lower alkyl, —OH, halo, lower alkoxy, trifluormethyl, nitro, or amino; $R_2$ is $C_2$-$C_5$ alkylene, alkenylene (cis or trans), or alkynylene, optionally substituted by at least one $C_1$-$C_6$ linear alkyl group, phenyl group or

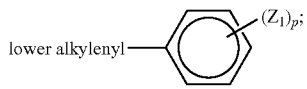

where $Z_1$ is lower alkyl, —OH, lower alkoxy, —$CF_3$, —$NO_2$, —$NH_2$, or halogen; $R_3$ is lower alkyl or hydrogen; $R_7$ is hydrogen, lower alkyl, or acyl; $R_8$ is lower alkyl; $R_9$ is hydroxy, lower alkoxy, or —$NHR_{10}$; $R_{10}$ is hydrogen, lower alkyl, $C_1$-$C_3$ acyl, aryl,

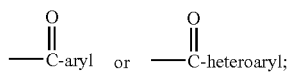

$X_1$, $X_2$, and $X_3$ are, independently, —O—, —S—, =N—, or —N($R_3$)—, or $X_1$ and $X_2$ are not covalently bound to each other and are, independently, —OH, =O, —$R_3$, or =$NR_3$; lower is 1-4 carbon atoms; m is 1, 2, or 3; and n is 1 or 2.

In some such compounds, R is —C(O)$CH_2$OH, —CH(OH)C(O)$CH_2$OH, —C(O)OH, CH(OH)$CH_3$, or C(O)$CH_3$; $R_1$ is halo; $X_1$ and $X_2$ are different and are =O, —OH, =N—, or —O—; $R_2$ is $C_2$-$C_4$ alkylene or alkenylene; $R_3$ is hydrogen, methyl, or ethyl; $X_3$ is —O—; and R is substituted as shown in Formula 1A (1A)

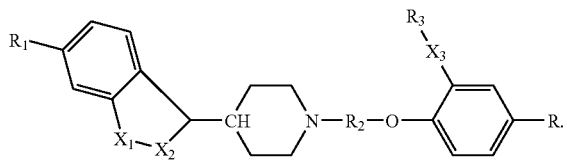

In some embodiments, the compound of Formula 1 is 1-[4-3-[4-(6-fluoro-1,2-benzisoxazol-3-yl)-1-piperidinyl]propoxy]-3-methoxyphenyl]ethanone, as shown in Formula 1 B:

(1B)

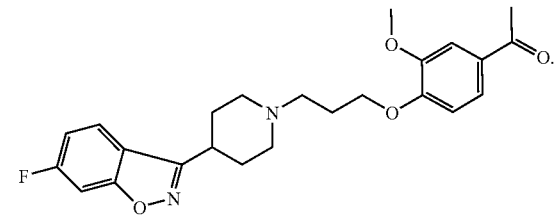

In still other embodiments, the compound of Formula 1 is 1-[4-[3-[4-(6-Fluoro-1,2-benzisoxazol-3-yl)-1-piperidinyl] propoxy]-3-methoxyphenyl]ethanol, as shown in Formula 10:

(1C)

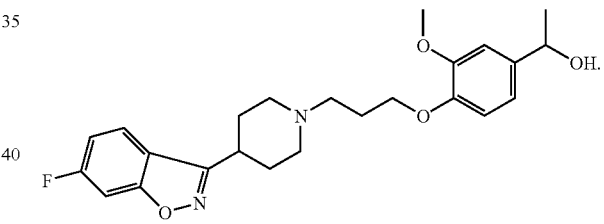

Using the genotypes at the SNP loci above, it is possible, with a high degree of certainty, to predict an individual's predisposition to QT prolongation. Table 2 below shows the results of a study of 174 individuals, each of whom was genotyped at the rs993648 locus and their QT interval measured following the oral administration of 24 mg/day B.I.D. of iloperidone for a period of two weeks.

TABLE 2

QT Prolongation and Presence or Absence of a Genotype for
SNP__A-4232718, rs993648 Associated with a Predisposition to QT Prolongation

| Change Threshold (msec) | Low QT | | High QT | | Odds Ratio | p value | sensitivity | specificity | negative predictive value | positive predictive value |
|---|---|---|---|---|---|---|---|---|---|---|
| | −test | +test | −test | +test | | | | | | |
| QT > 5 | 42 | 22 | 38 | 72 | 3.62 | 0.0001 | 0.65 | 0.66 | 0.53 | 0.77 |
| QT > 15 | 62 | 41 | 18 | 53 | 4.45 | <0.0001 | 0.75 | 0.60 | 0.78 | 0.56 |
| QT > 30 | 76 | 71 | 4 | 23 | 6.16 | 0.0013 | 0.85 | 0.52 | 0.95 | 0.24 |

As can be seen in Table 2, an individual's CERKL sequence at the SNP_A-4232718, rs993648 locus is highly predictive of whether the individual will experience QT prolongation following the administration of iloperidone. For example, using the lowest threshold of a change in QTc interval (between baseline and the end of the second week) greater than 5 milliseconds (normal QTc intervals are between 0.30 and 0.44 seconds for males and between 0.30 and 0.45 for females), 72 of those individuals with a SNP genotype (test is considered positive if genotype for SNP_A-4232718, rs993648 is non-AB) associated with a predisposition to QT prolongation experienced QT prolongation while only 22 such individuals did not. Similarly, nearly twice as many individuals (72) experiencing QT prolongation possessed a SNP genotype associated with a predisposition to QT prolongation as did not (38). This resulted in a sensitivity (probability that the individual will have a SNP genotype associated with a predisposition to QT prolongation, given that he/she experienced QT prolongation) of 0.65 and a specificity (probability that the individual will not have a SNP genotype associated with a predisposition to QT prolongation, given that he/she did not experience QT prolongation) of 0.66, a negative predictive value (probability that the individual will not experience QT prolongation, given that he/she does not have a SNP genotype associated with a predisposition to QT prolongation) of 0.53, and a positive predictive value (probability that the individual will experience QT prolongation, given that he/she has a SNP genotype associated with a predisposition to QT prolongation) of 0.77.

The use of higher thresholds (i.e., QTs greater than 15 and 30 milliseconds) yielded markedly increased negative predictive values (0.78 and 0.95, respectively). The associated decrease in positive predictive values, from 0.77 for QTs greater than 5 milliseconds to 0.24 for QTs greater than 30 milliseconds) suggests that additional factors affect more severe QT prolongation.

As the data in Table 2 show, an individual's CERKL sequence at the SNP loci above may be used to predict whether an individual is predisposed to QT prolongation due to the administration of a compound capable of prolonging the QT interval. That is, individuals having one or more SNP genotype associated with a predisposition to QT prolongation may reliably be predicted to experience a prolonged QT interval (i.e., a QT interval prolonged by at least 5 milliseconds) following the administration of a compound capable of prolonging the QT interval. Similarly, individuals not having any of the above SNP genotypes associated with a predisposition to QT prolongation may reliably be predicted to not experience severe QT prolongation (i.e., a QT interval prolonged greater than 15 milliseconds) following the administration of a compound capable of prolonging the QT interval.

The ability to make such predictions may be used in deciding whether to treat an individual with a particular compound and/or in determining the dosage appropriate for the individual. For example, an individual predicted to experience QT prolongation may be treated with an alternative compound not known or suspected to cause QT prolongation or may be administered a lower dose of a compound capable of causing QT prolongation than would be administered to an individual not predicted to experience QT prolongation.

The present invention also includes the administration of another compound useful in treating LQTS, in addition to one or more of the compounds above. Compounds useful in treating LQTS and/or preventing cardiac events resulting from LQTS, include, for example, beta blockers, such as propranolol, nadolol, atenolol, metoprolol.

The present invention also includes the prediction of an individual's predisposition for QT prolongation based on one or more of the SNP loci above in combination with the individual's genotype or gene sequence at one or more additional genes or loci. For example, International Patent Application Publication No. WO2006039663, incorporated herein by reference, describes a method of treating an individual with a compound capable of inducing QT prolongation based on the individual's CYP2D6 genotype. Other genotypes and/or gene sequences may similarly be used in combination with the SNP loci above, including those associated with LQTS.

Multiple techniques for determining the sequence of the CERKL gene or of one or more portions thereof (including, e.g., the following SNPs: rs895901, rs1441162, rs993650, rs993648, rs16867450, rs16867452, rs6433927) are well known in the art. These include amplifying and sequencing genomic or complementary DNA or mRNA as well as, e.g., hybridization techniques.

After determining the genotype across the entire CERKL gene or a portion of it, such as the SNPs identified above, the patient's genotype can be compared to genotypes described above as being associated with prolonged QT prolongation. Thus, e.g., if a given individual's genotype at rs993648 is other than A in one gene and G in the second copy of that gene, then, with reference to Table 1, one can see that that person is predisposed to prolonged QT interval.

In one practice of the invention, a person or other entity performing a genotyping test for an individual's CERKL gene will determine the genotype only for one or more of single nucleotide polymorphism (SNP) loci selected from the group consisting of: rs895901, rs1441162, rs993650, rs993648, rs16867450, rs16867452, and rs6433927. In a related practice of the invention, a person or other entity that performs such genotype assay will determine the person's genotype at one or more of said loci and will report the person's genotype only at such one or more of said loci.

It should also be understood that the present invention includes the characterization of an expression product of the CERKL gene rather than, or in addition to, the determination of one or more SNP genotypes within the CERKL gene. For example, by determining a sequence of an mRNA strand transcribed from the CERKL gene, it is possible to determine the sequence of the CERKL gene itself and, as described above, determine whether the CERKL gene sequence is associated with a predisposition to QT prolongation.

Similarly, by properly characterizing a peptide or protein, including the CERKL enzyme, translated from the mRNA strand above, it is possible to determine the sequence of the CERKL gene itself and, as described above, determine whether the CERKL gene sequence is associated with a predisposition to QT prolongation.

Phenotypic assays that indirectly determine a person's CERKL genotype are described, e.g., with respect to CYP2D6 alleles, by Leyland-Jones, US20030170176.

This invention encompasses kits and reagents for determining an individual's CERKL genotype, including, e.g., probes and primers. Kits of the invention include reagents and, optionally, other materials, useful in determining an individual's genotype for the CERKL gene. Such kit may include, e.g., a detection means, a collection device, containers, and instructions, and may be used in determining a patient's CERKL genotype, such as for determining an appropriate treatment strategy for a person having a disorder for which iloperidone is indicated. Such treatment strategy might comprise, e.g., choosing a different drug, i.e., one not associated with QT prolongation, adjusting the dose of iloperidone, or monitoring the patient during treatment for prolonged QT interval.

Detection means may detect a CYP2D6 polymorphism directly or indirectly via mRNA or protein. Such detection means may also indirectly determine genotype at a relevant loci by taking advantage of linkage disequilibrium with another polymorphism. Detection means include, e.g., polynucleotides used in amplification, sequencing and SNP detection techniques, Invader(R) assays (Third Wave Technologies Inc.), Taqman(R) assays (Applied Biosystems, Inc.) gene chip assays (such as those available from Affymetrix, Inc.), pyrosequencing, fluorescence resonance energy transfer (FRET)-based cleavage assays, fluorescent polarization, denaturing HPLC, mass spectometry, and polynucleotides having fluorescent or radiological tags used in amplification and sequencing.

Collection devices suitable for use in the invention include devices known in the art for collecting and/or storing a biological sample of an individual from which nucleic acids and/or polypeptides can be isolated. Such biological samples include, for example, whole blood, semen, saliva, tears, urine, fecal material, buccal smears, skin, hair, and biopsy samples. Accordingly, suitable collection devices include, for example, specimens cups, swabs, glass slides, test tubes, lancets, and Vacutainer(R) tubes and kits.

An illustrative embodiment of a kit of the invention is a kit that comprises a set of oligonucleotides, wherein each member of the set selectively, hybridizes to regions of selected variants of the CERKL gene that comprise one or more SNPs selected from the group consisting of: rs895901, rs1441162, rs993650, rs993648, rs16867450, rs16867452, and rs6433927. By "selectively hybridizes," one of skill in the art would understand that the oligonucleotide will hybridize preferentially for a given SNP genotype such that the nucleotide in that SNP locus can be determined. Such oligonucleotides can be provided, e.g., in the form of an array of nucleic acid molecules attached to a support, wherein the array has oligonucleotides that will hybridize to selected allelic variants, or SNPs, of CERKL, such as, e.g., rs993648.

Such nucleic acids of the invention can be used, for e.g., in prognostic methods, such as are described herein. Specifically, for example, the nucleic acids of the invention can be used as probes or primers to determine whether a subject has a genotype for the CERKL gene that is associated with predisposition to QT prolongation.

Assays for determining genotype for the CERKL gene can be done in many clinical laboratories, such as those found in a typical hospital, clinic and private reference laboratories. In accordance with an aspect of this invention, kits are designed that contain some or all the reagents, primers and solutions for the genotyping assay.

An illustrative assay for determining an individuals CERKL genotype comprises: a) obtaining a genomic DNA sample of said subject; b) using the DNA sample of step a), amplifying a fragment comprising a polymorphic site of the CYP2D6 genes; c) hybridizing the amplified fragment of step b) with allele-specific oligonucleotides probes corresponding to wild type and variant alleles to determine the CYP2D6 genotype of the subject. Such methods include methods that are well known, such as are disclosed by Milos et al., US20030170176, Huang, US20040091909, Neville, et al., US20040096874, WO03544266, and WO03038123.

In addition, the present invention includes determining whether a compound is capable of prolonging a QT interval in an individual. This may be done, for example, by measuring a change in QT interval in a test organism (e.g., human, animal model, cell line) known to possess a CERKL genotype associated with a predisposition to QT prolongation following the administration of a quantity of compound under study. Preferably, the compound is also administered to a test organism known to possess a CERKL genotype not associated with a predisposition to QT prolongation.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09074254B2). An electronic copy of the "Sequence Listing" will also be available from the USPTO upon request and payment of the fee set forth in 37 CFR 1.19(b)(3).

What is claimed is:

1. A method of administering a compound to a human individual, the method comprising:

determining, or having determined, from a biological specimen obtained from the individual, the individual's genotype at the single nucleotide polymorphism (SNP) locus rs993648;

in the case that the individual's genotype at the rs993648 locus is AG and not associated with an increased risk of QT prolongation, administering to the individual a first quantity of iloperidone, an iloperidone metabolite, or a pharmaceutically-acceptable salt thereof; and in the case that the individual's genotype at the rs993648 locus is non-AG and associated with an increased risk of QT prolongation, administering to the individual a second quantity of iloperidone, an iloperidone metabolite, or a pharmaceutically-acceptable salt thereof that is less than the first quantity that would be administered to an individual having an AG genotype at the rs993648 locus.

2. The method of claim 1, further comprising:

determining the individual's CYP2D6 genotype.

3. A method of administering a compound capable of prolonging a QT interval to a human individual suffering from long QT syndrome (LQTS), the method comprising:

determining the individual's genotype at the single nucleotide polymorphism (SNP) locus rs993648; and administering to the individual a quantity of iloperidone, an iloperidone metabolite, or a pharmaceutically-acceptable salt thereof based on the individual's genotype at the rs993648 locus, wherein an individual determined to have an AG genotype at the rs993648 locus is administered 24 mg/day of iloperidone, an iloperidone metabolite, or a pharmaceutically-acceptable salt thereof and an individual determined to have a non-AG genotype at the rs993648 locus is administered less than 24 mg/day of iloperidone, an iloperidone metabolite, or a pharmaceutically-acceptable salt thereof.

4. The method of claim 3, further comprising:
determining the individual's CYP2D6 genotype.

5. The method of claim 1, wherein the first quantity is 24 mg/day.

6. The method of claim 1, wherein the individual is suffering from long QT syndrome (LQTS).

* * * * *